(12) United States Patent  
Shelley et al.

(10) Patent No.: US 8,734,411 B2
(45) Date of Patent: May 27, 2014

(54) MULTI-LAYER ODOR BARRIER TUBE, AND COMBINATION ODOR BARRIER TUBE AND ODOR BARRIER COLLECTION BAG

(75) Inventors: Phil Shelley, Highwood, IL (US); Seamus T. Kavanagh, Libertyville, IL (US); Claudio Giori, Riverwoods, IL (US); Deepak Prakash, Lake Zurich, IL (US); Adel Sadik, Fox River Grove, IL (US); Rick Hantke, Chicago, IL (US); Kimberly R. Hansford, Winthrop Harbor, IL (US)

(73) Assignee: Hollister Incorporated, Libertyville, IL (US)

( * ) Notice: Subject to any disclaimer, the term of this patent is extended or adjusted under 35 U.S.C. 154(b) by 764 days.

(21) Appl. No.: 12/238,584

(22) Filed: Sep. 26, 2008

(65) Prior Publication Data

US 2009/0088711 A1 Apr. 2, 2009

Related U.S. Application Data

(60) Provisional application No. 60/976,214, filed on Sep. 28, 2007.

(51) Int. Cl.
*A61F 5/441* (2006.01)
*A61F 5/44* (2006.01)

(52) U.S. Cl.
USPC ............................................ 604/326; 604/333

(58) Field of Classification Search
USPC .................................................. 604/326–328
See application file for complete search history.

(56) References Cited

U.S. PATENT DOCUMENTS

| 2,800,145 | A | 7/1957 | Peierls et al. | |
| 3,561,493 | A | 2/1971 | Maillard | 138/141 |
| 4,312,693 | A | 1/1982 | Salensky et al. | |
| 4,376,799 | A | 3/1983 | Tusim | |
| 4,445,898 | A | 5/1984 | Jensen | 604/337 |
| 4,627,844 | A | 12/1986 | Schmitt | 604/264 |
| 4,650,817 | A | 3/1987 | Allen, Jr. et al. | 523/105 |
| 4,687,711 | A | 8/1987 | Vietto et al. | |
| 4,721,508 | A | 1/1988 | Burton | |

(Continued)

FOREIGN PATENT DOCUMENTS

| EP | 0 366 802 A1 | 5/1990 |
| EP | 0 469 926 | 2/1992 |

(Continued)

OTHER PUBLICATIONS

EXACT plastomers, http://www.exxonmobilchemical.com/, printed Sep. 18, 2013.*

(Continued)

*Primary Examiner* — Susan Su
(74) *Attorney, Agent, or Firm* — Lempia Summerfield Katz LLC

(57) ABSTRACT

A multi-layer odor barrier catheter tube for a fecal drainage catheter. The external surface has a low coefficient of friction, as does the internal surface. The layers of the catheter tube may be co-extruded, or formed as a heat-laminated film rolled into a cylindrical shape and heat-welded. A flexible scrim may be included intermediate the first and third layers. One or more tie layers may be included between at least one of the first and second layers, or the second and third layers. A combination of a multi-layer odor barrier catheter tube with an odor barrier collection bag is also described.

9 Claims, 6 Drawing Sheets

(56) References Cited

U.S. PATENT DOCUMENTS

| | | | |
|---|---|---|---|
| 4,778,553 A | 10/1988 | Wood et al. | |
| 4,906,495 A | 3/1990 | Martini et al. | |
| 5,084,315 A | 1/1992 | Karimi et al. | |
| 5,171,305 A | 12/1992 | Schickling et al. | |
| 5,261,898 A | 11/1993 | Polin et al. | |
| 5,277,753 A | 1/1994 | Kelley et al. | |
| 5,290,613 A | 3/1994 | Shuetz et al. | |
| 5,356,400 A * | 10/1994 | Temple | 604/356 |
| 5,356,709 A | 10/1994 | Woo et al. | 428/376 |
| 5,364,662 A | 11/1994 | Domenico et al. | |
| 5,386,817 A | 2/1995 | Jones | |
| 5,407,713 A | 4/1995 | Wilfong et al. | |
| 5,439,454 A | 8/1995 | Lo et al. | 604/264 |
| 5,439,545 A | 8/1995 | Nakanishi et al. | |
| 5,466,424 A | 11/1995 | Kusano et al. | |
| 5,468,526 A | 11/1995 | Allen et al. | 428/35.4 |
| 5,470,624 A | 11/1995 | Oreglia et al. | 428/36.1 |
| 5,480,377 A | 1/1996 | Cartmell et al. | 602/48 |
| 5,488,975 A | 2/1996 | Chiles et al. | |
| 5,496,295 A | 3/1996 | Wilfong et al. | |
| 5,529,820 A | 6/1996 | Nomi et al. | |
| 5,567,488 A | 10/1996 | Allen et al. | |
| 5,567,489 A | 10/1996 | Allen et al. | 428/34.1 |
| 5,569,216 A | 10/1996 | Kim | |
| 5,643,375 A | 7/1997 | Wilfong et al. | |
| 5,681,627 A * | 10/1997 | Mueller | 428/35.2 |
| 5,686,173 A | 11/1997 | Fujii et al. | 428/213 |
| 5,730,919 A | 3/1998 | Wilfong et al. | |
| 5,738,923 A | 4/1998 | Ko et al. | 428/36.91 |
| 5,759,173 A | 6/1998 | Preissman et al. | |
| 5,908,656 A | 6/1999 | Ishikawa et al. | |
| 5,928,744 A * | 7/1999 | Heilmann et al. | 428/36.6 |
| 5,932,307 A | 8/1999 | Ryan et al. | 428/36.9 |
| 5,983,604 A | 11/1999 | Wilfong et al. | |
| 5,986,003 A | 11/1999 | Lee et al. | |
| 6,050,982 A | 4/2000 | Wheeler | |
| 6,057,414 A | 5/2000 | Razavi | |
| 6,136,394 A | 10/2000 | Karsten | 428/35.7 |
| 6,143,383 A | 11/2000 | Giori | 428/35.2 |
| 6,165,166 A * | 12/2000 | Samuelson et al. | 604/524 |
| 6,217,547 B1 | 4/2001 | Lee | 604/96.01 |
| 6,258,423 B1 | 7/2001 | Giori | 428/36.7 |
| 6,286,555 B1 | 9/2001 | Pauker et al. | |
| 6,299,596 B1 | 10/2001 | Ding | |
| 6,406,767 B1 | 6/2002 | Mueller | 428/36.91 |
| 6,431,219 B1 | 8/2002 | Redler et al. | 138/137 |
| 6,447,835 B1 | 9/2002 | Wang et al. | |
| 6,455,161 B1 | 9/2002 | Regnier et al. | |
| 6,620,474 B1 | 9/2003 | Regnier et al. | 428/35.7 |
| 6,663,614 B1 * | 12/2003 | Carter | 604/525 |
| 6,770,342 B2 | 8/2004 | Buongiorno | |
| 6,776,195 B2 | 8/2004 | Blasko et al. | 138/141 |
| 6,869,653 B2 * | 3/2005 | Ling et al. | 428/36.9 |
| 6,945,970 B2 | 9/2005 | Pepin | 604/525 |
| 6,964,816 B2 | 11/2005 | Schell et al. | 428/474.4 |
| 6,977,105 B1 | 12/2005 | Fujieda et al. | 428/36.9 |
| 7,015,284 B2 | 3/2006 | Ajbani et al. | |
| 7,090,664 B2 | 8/2006 | Holter | |
| 7,100,767 B2 | 9/2006 | Chomik et al. | |
| 7,112,298 B2 | 9/2006 | Kampa et al. | |
| 7,147,627 B2 | 12/2006 | Kim et al. | |
| 7,270,860 B2 | 9/2007 | Giori | |
| 7,361,170 B2 | 4/2008 | Williams et al. | |
| 7,396,582 B2 | 7/2008 | Claude et al. | |
| 7,481,804 B2 | 1/2009 | Devens, Jr. | |
| 7,550,185 B2 | 6/2009 | Ling et al. | |
| 7,628,784 B2 | 12/2009 | Diaz et al. | |
| 7,647,949 B2 | 1/2010 | Donohue et al. | |
| 7,722,583 B2 | 5/2010 | Kim et al. | |
| 8,323,254 B2 * | 12/2012 | Tsai et al. | 604/317 |
| 8,399,077 B1 * | 3/2013 | Bekele | 428/35.2 |
| 2002/0016607 A1 | 2/2002 | Bonadio et al. | 606/192 |
| 2003/0064182 A1 | 4/2003 | Giori | 428/35.2 |
| 2003/0131569 A1 | 7/2003 | Chomik et al. | |
| 2003/0218022 A1 | 11/2003 | Chomik et al. | |
| 2004/0134555 A1 | 7/2004 | Powell et al. | 138/141 |
| 2004/0175525 A1 | 9/2004 | Willard et al. | 428/36.91 |
| 2004/0228992 A1 | 11/2004 | Giori | 428/35.7 |
| 2005/0038374 A1 | 2/2005 | Williams, Jr. et al. | |
| 2005/0054996 A1 | 3/2005 | Gregory | |
| 2005/0075616 A1 | 4/2005 | Holter | |
| 2005/0182387 A1 * | 8/2005 | Webler | 604/527 |
| 2005/0273064 A1 | 12/2005 | Dircks et al. | 604/322 |
| 2006/0147698 A1 | 7/2006 | Carroll et al. | 428/316.6 |
| 2006/0249418 A1 | 11/2006 | Chomik et al. | 206/524.1 |
| 2006/0253102 A1 * | 11/2006 | Nance et al. | 604/525 |
| 2007/0043333 A1 | 2/2007 | Kampa et al. | |
| 2007/0051418 A1 | 3/2007 | Rowles et al. | |
| 2008/0032110 A1 * | 2/2008 | Wood et al. | 428/220 |
| 2008/0103463 A1 | 5/2008 | Tsai et al. | 604/317 |
| 2008/0262447 A2 | 10/2008 | Martino et al. | |
| 2009/0048537 A1 | 2/2009 | Lydon et al. | |
| 2009/0088711 A1 | 4/2009 | Shelley et al. | |
| 2009/0169788 A1 | 7/2009 | Pandey et al. | |
| 2009/0202759 A1 | 8/2009 | O'Brien et al. | |
| 2009/0240235 A1 | 9/2009 | Murata | |
| 2010/0055357 A1 | 3/2010 | Ciccarello | |
| 2010/0055367 A1 | 3/2010 | Ohigawa | |
| 2010/0063477 A1 | 3/2010 | Ohigawa | |
| 2010/0174252 A1 | 7/2010 | Tanghoej et al. | |
| 2010/0274201 A1 | 10/2010 | Feeley et al. | |

FOREIGN PATENT DOCUMENTS

| | | | |
|---|---|---|---|
| EP | 0 575 798 A1 | 12/1993 | |
| EP | 0 615 832 A1 | 9/1994 | |
| EP | 0 913 165 B1 | 5/1999 | |
| EP | 1 514 572 A2 | 3/2005 | |
| JP | 54-074514 A | 6/1979 | |
| JP | 3-041176 A | 2/1991 | |
| JP | 3-050262 A | 3/1991 | |
| JP | 4-100857 A | 4/1992 | |
| JP | 2001-227682 A | 8/2001 | |
| WO | WO-99/23158 A1 | 5/1999 | |
| WO | WO-01/83017 A1 | 1/2001 | |
| WO | WO 2008/052018 A2 | 5/2008 | |

OTHER PUBLICATIONS

Polyolefin Elastomers, http://www.iisrp.com/WebPolymers/05ModPolyolefineElast_v1-2.pdf, Mar. 11, 2006.*

PolyOne GLS Thermoplastic Elastomers Frequently Asked TPE Questions, http://www.glstpes.com/resources_faqs.php, printed Sep. 18, 2013.*

International Search Report of PCT/US2008/077796, mailed Dec. 23, 2008 (5 pages).

Written Opinion of PCT/US2008/077796, mailed Dec. 23, 2008 (8 pages).

Lai et al., "Surface Modification of Silicone Rubber by Gas Plasma Treatment," *J. Adhesion Sci. Technol.*, 10(3):231-242 (1996).

* cited by examiner

MULTI-LAYER ODOR BARRIER TUBE, AND COMBINATION ODOR BARRIER TUBE AND ODOR BARRIER COLLECTION BAG

REFERENCE TO RELATED APPLICATIONS

This application claims the benefit of the filing date of U.S. Provisional Application No. 60/976,214, filed Sep. 28, 2007.

FIELD OF THE DISCLOSURE

This disclosure is generally directed to medical tubing and, more specifically, to multi-layered tubing having odor barrier properties suitable for use as catheter tubing for fecal drainage systems, and a combination odor barrier tube and odor barrier collection bag.

BACKGROUND

Catheter tubes for fecal drainage systems are designed to facilitate flow of fecal matter, with the fecal matter typically draining into a collection bag. A catheter tube can include a lubricious coating on an interior to facilitate movement of fecal matter. While various materials have been used to form the walls of a catheter tube, no catheter tubes for fecal drainage systems are known that include integral odor barrier properties. One reason for the lack of catheter tubes having odor barrier properties is that odor barrier materials are understood to be too stiff and not suitable for catheter tubing applications. By providing a multi-layer catheter tube with at least one odor barrier layer, the catheter tube can reduce or eliminate exposure of the patient, caregivers, and other persons in the vicinity of the patient to unpleasant odors.

Fecal drainage systems are frequently employed in combination with enema, lavage, or other irrigation techniques to loosen stool in the rectum of a patient. As a result, water or other liquid is likely to travel through the catheter tube with fecal matter.

SUMMARY OF THE DISCLOSURE

In preferred embodiments of the present disclosure, the catheter tubing for a fecal drainage system is made of at least two layers of different materials. The layers are preferably co-extruded, or one layer may be extruded and one or more subsequent layers may subsequently be applied by extrusion over the first layer, but alternately, the layers may be formed as a generally flat laminate sheet that is rolled into a tubular shape, then sealed along a seam, for example using sealing technology, such as heat sealing or RF sealing, using adhesive sealing, or ultrasonic welding. In order to increase durability, at least one of the layers of the flat laminate sheet that is then rolled into a cylinder can be a semi-rigid mesh or scrim material.

Another desirable feature of a catheter tube for a fecal drainage system is minimal wall thickness. The multi-layer odor barrier catheter tube of the present disclosure can be manufactured with a total wall thickness in the range of about 10 mil to about 60 mil.

The odor barrier layer may be a resin, preferably a polyamide, and most preferably nylon 666. The odor barrier layer may include an additive in the form of a modifier for reduced modulus, preferably ethylene-ethylacrylate-maleic anhydride terpolymer (commercially available as Lotader® 4720, from Arkema, Inc. of Philadelphia, Pa.). The odor barrier layer is preferably the outermost layer, or outer skin, of the catheter tube.

The odor barrier layer of the catheter tube preferably has a thickness of 3 mil or less, and the thickness of the odor barrier is preferably less than 30% of the total tube wall thickness. The odor barrier layer preferably has a kinetic coefficient of friction less than 0.5.

A second layer of the catheter tube may be a resin or resin blend, preferably having a modulus of elasticity less than 100,000 psi (2% secant) when measured according to ASTM D882.

A third layer forming the innermost layer or inner skin of the catheter tube may also be employed. The third or innermost layer preferably has a low kinetic coefficient of friction, preferably less than 0.5. The low kinetic coefficient of friction may be an inherent property of a dry material of which the third layer is formed. Lubricity is a beneficial feature of the innermost layer of the catheter tube to promote or facilitate flow of fecal matter through the catheter tube. In order to achieve the desired lubricity of the innermost surface of the catheter tube, the inner layer of the multi-layer odor barrier tube of the present disclosure may be made of a copolymer of ethylene, preferably an ethylene vinylacetate copolymer (EVA) with an added slip agent concentrate, such as 10090 Slip PE MB, having a concentration of 5% Erucamide, available from Ampacet of Tarrytown, N.Y., to lower the coefficient of friction. Preferably, the slip agent concentrate is only about 2% of the overall composition of the innermost layer of the catheter tube, so the effective concentration of the Erucamide is about 0.1%.

In light of the likely presence of water or other liquid traveling through the catheter tube with the fecal matter, as an alternative to an EVA copolymer, a hydrophilic polymer that becomes lubricious in contact with water, preferably polyethyleneoxide or polyvinylalcohol, may be used as the inner layer of the multi-layer odor barrier catheter tube.

If the collection bag into which the catheter tube drains lacks odor barrier properties, unpleasant odors can escape the collection bag, thereby negating the odor barrier benefits achieved by the odor barrier catheter tube. It is therefore desirable for the odor barrier tube to drain into a collection bag that itself has odor barrier walls.

DETAILED DESCRIPTION OF THE PREFERRED EMBODIMENTS

With reference to the drawings, in a first embodiment of a multi-layer odor barrier catheter tube 10 of the present disclosure connectable at a first end to a patient-proximal internal section, and/or a trans-anal section of a rectal catheter (not shown), and at a second end, connectable to a waste collection bag or to a disposal receptacle (e.g., a bedpan or toilet (not shown)) is provided. At least one of the layers of the multi-layer catheter tube 10 is constructed of materials resistant to transmission of fecal and flatus gasses.

A first layer 12 of the catheter tube 10 defines the external surface 14 of the catheter tube 10. The first layer 12 is preferably comprised of one or more materials that possess a relatively low coefficient of friction, most preferably less than 0.5, so as to reduce drag of the catheter tube 10 against a patient's skin, and against items surrounding the patient, including a hospital gown, bed sheets, chair or other objects in the patient's immediate vicinity. The low coefficient of friction of the external surface 14 of the catheter tube 10 also facilitates "milking" the fecal matter down the length of the catheter tube 10. The material or materials defining the first layer 12 of the catheter tube 10 include an odor barrier resin. In other embodiments within the scope of the present disclosure, the odor barrier resin may be employed as a layer of the catheter tube 10 other than the first layer 12 defining the outside surface 14.

A suitable material for the first layer 12 of the catheter tube 10 of the present disclosure is a polyamide, most preferably nylon 666. A modifier may be added to achieve a reduced modulus, preferably ethylene-ethylacrylate-maleic anhydride terpolymer, commercially available as Lotader® 4720 from Arkema, Inc. The external surface 14 of the first layer 12 is preferably a surface that will receive inks such as permanent or semi-permanent markers, and retain such markings thereon without smudging or wiping off, to facilitate receiving instructions, patient data, collection bag change data, dates of indwell or intended removal of the catheter tube, and the like.

Figure 10:
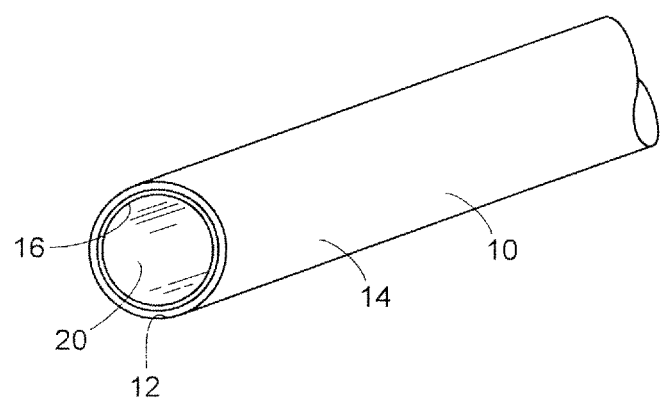
FIG. 10 is a front perspective view of a multi-layer odor barrier catheter tube of the present disclosure having only two layers.

An intermediate layer 16 of the multi-layer catheter tube 10 preferably comprises a resin or resin blend having a modulus of elasticity less than 100,000 psi (2% secant) when measured according to ASTM D882. The resin used as the material forming the intermediate layer 16 is preferably a thermoplastic elastomer, most preferably polyurethane or a polyurethane blended with another thermoplastic elastomer, having a preferred modulus less than 40,000 psi (2% secant). As described in more detail below, more than one layer of material may be provided intermediate the first layer 12 defining the external surface 14 of the catheter tube 10 and a third layer 18 defining an internal surface 20 of the catheter tube 10. If only a first layer 12 and a low modulus layer are provided, the layer referenced herein as the intermediate layer 16 may instead be the inner-most layer of the catheter tube 10, as shown in FIG. 10.

Figure 1:
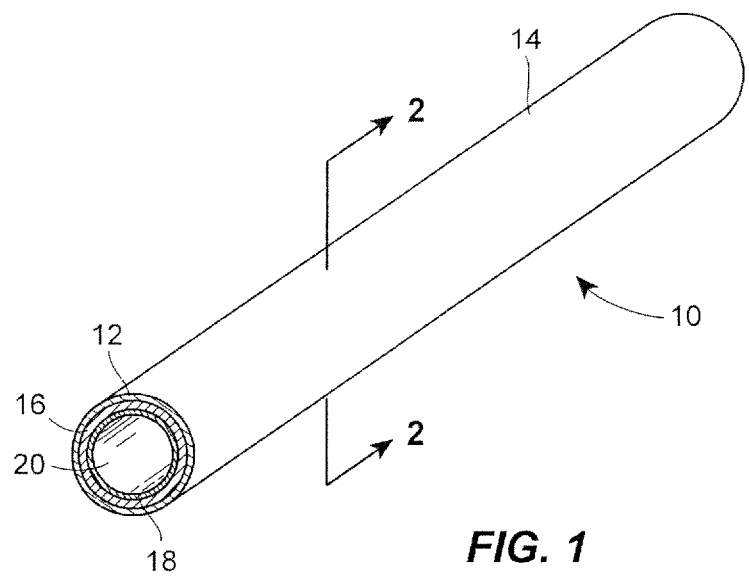
FIG. 1 is a perspective view of a first embodiment of a multi-layer odor barrier catheter tube of the present disclosure.
Figure 2:
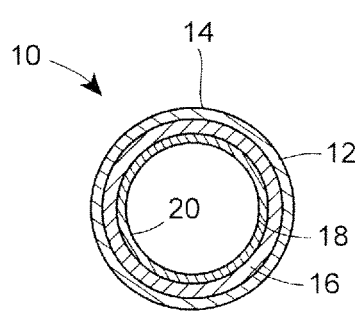
FIG. 2 is an axial cross-sectional view, taken along lines 2-2 of FIG. 1.
Figure 3:
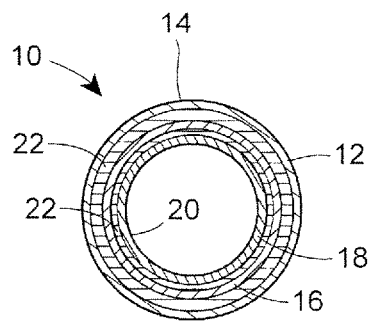
FIG. 3 is an axial cross-sectional view, similar to FIG. 2, of a second embodiment of a multi-layer odor barrier catheter tube of the present disclosure, wherein tie layers are provided between the first and second layers, and between the third and fourth layers.

Depending on the compatibility of the materials of adjacent layers of the multi-layered catheter tube 10, as shown in FIG. 3, a tie layer 22, such as a Bynel® tie material available from DuPont, may be employed between adjacent layers to improve adhesion of the adjacent layers to one another.

Another layer 18 of the multi-layer catheter tube 10, defining the internal surface 20 of the catheter tube 10, is preferably made of one or more materials that possess a relatively low coefficient of friction, preferably less than 0.5, to allow stool and bowel discharge to flow easily along the internal length of the catheter tube 10 for collection and/or disposal. A suitable material for the layer 18 is a copolymer of ethylene, most preferably an ethylene-vinylacetate copolymer (EVA) with an added slip agent (such as 10090 Slip PE MB, having a concentration of 5% Erucamide, available from Ampacet of Tarrytown, N.Y.), wax, PTFE, or other friction-reducing additive to achieve a low coefficient of friction. Such additives may also be used to lower the coefficient of friction of the first layer 12 defining the external surface 14 of the catheter tube 10. As an alternate to the material or materials defining the layer 18 of the catheter tube 10 inherently possessing a low coefficient of friction, a hydrophilic polymer that becomes lubricious in contact with water, preferably polyethyleneoxide or polyvinylalcohol, may be used as the innermost layer of the multi-layer odor barrier catheter tube 10. This may be accomplished by the layer 18 having a capability of anchoring hydrophilic materials thereto, and then supplying an additional hydrophilic layer, such as by co-extrusion, internally of the layer 18. As a further alternate, the layer 18 may itself be formed entirely of a hydrophilic polymer, and anchored directly to intermediate layer 16, provided that there is adequate adhesion between the hydrophilic layer 18 and the intermediate layer 16.

The multi-layer catheter tube 10 of the first embodiment of the present disclosure may be manufactured by co-extrusion. In order to maximize tube softness and flexibility, it is desirable for the odor barrier layer of the catheter tube 10 to be thin, preferably in a range of less than about 2 to about 3 mils.

Figure 4:
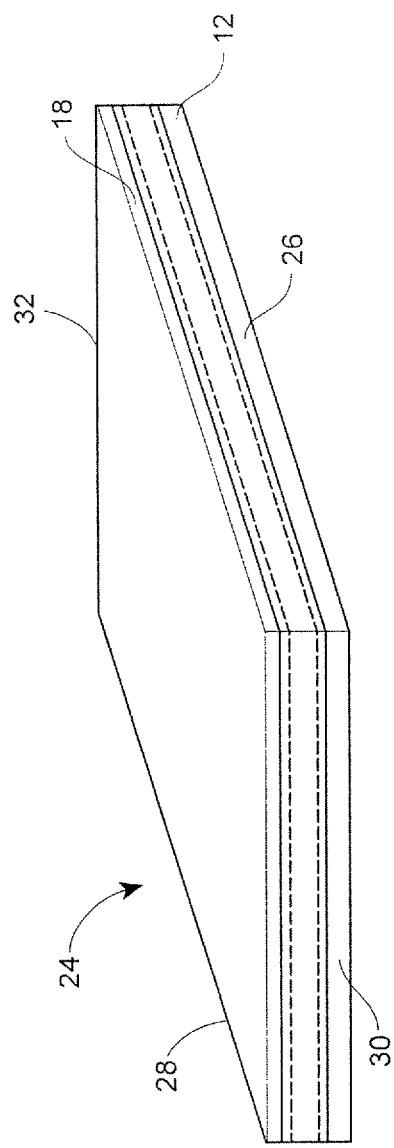
FIG. 4 is a perspective view of a heat-laminated film employed in a method of manufacture of a multi-layer odor barrier catheter tube of the present disclosure.
Figure 5:
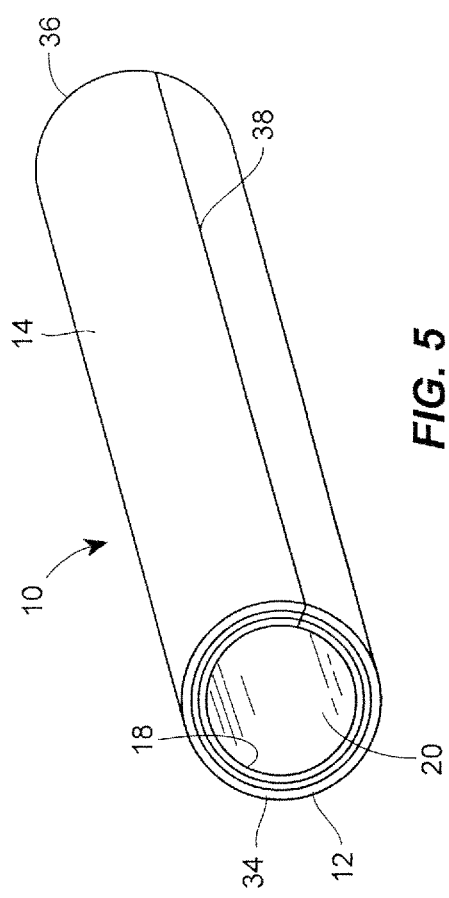
FIG. 5 is a perspective view of the heat-laminated film of FIG. 4, rolled into a cylindrical shape and sealed along a seam.

As an alternative to co-extrusion, as shown in FIGS. 4-5, the layers of the catheter tube 10 may be formed into a flat or substantially flat heat-laminated film 24, having two parallel edges 26, 28 that are rolled toward one another, brought into register with one another, and sealed to one another, such as by heat sealing, RF sealing, adhesive sealing, or ultrasonic welding, to form a cylinder, with the first layer 12 of the film 24 defining an external surface 14 of the cylinder and the third layer 18 defining an internal surface 20 of the cylinder. A leading end 30 and a trailing end 32 of the heat-laminated film 24 are left open, forming first and second ends 34, 36 of the catheter tube 10. Optionally, tie layers (represented by broken lines in FIG. 4) may be provided to enhance bonding between the first and second layers, and/or between the second and third layers 16, 18. The first, second and third layers 12, 16, 18 of the catheter tube 10 are preferably clear or translucent. The sealed edge or seam 38 may be visible, and can advantageously provide a medical caregiver with a visible indicator of any kinking or twisting of the catheter tube.

The total cumulative wall thickness of the multi-layer catheter tube 10 is preferably in the range of about 10 mil to about 40 mil, and more preferably in a range of about 25 mil to about 35 mil, with the thickness of the odor barrier layer (e.g., the first layer 12) making up less than about 30% of the total wall thickness of the catheter tube 10.

Adjustments may be made to process conditions under which the layers of the multi-layer catheter tube of the present disclosure are co-extruded or heat laminated to reduce the coefficient of friction of one or more of the layers.

Figure 6:
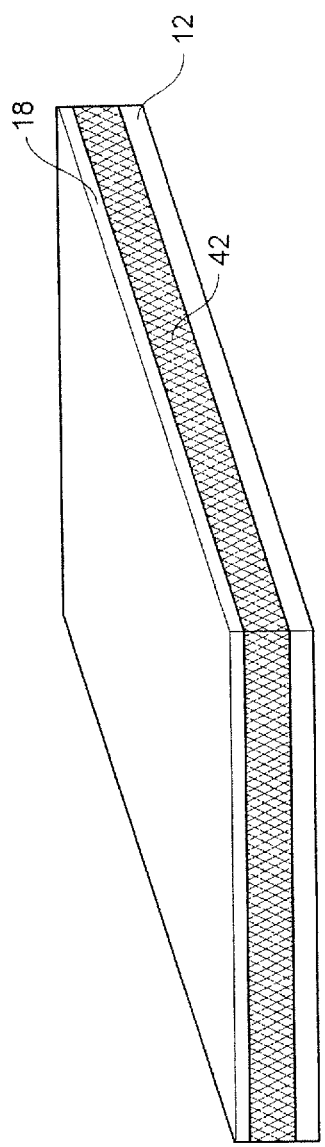
FIG. 6 is a perspective view of a heat-laminated film similar to that of FIG. 4, and including a flexible scrim layer.
Figure 7:
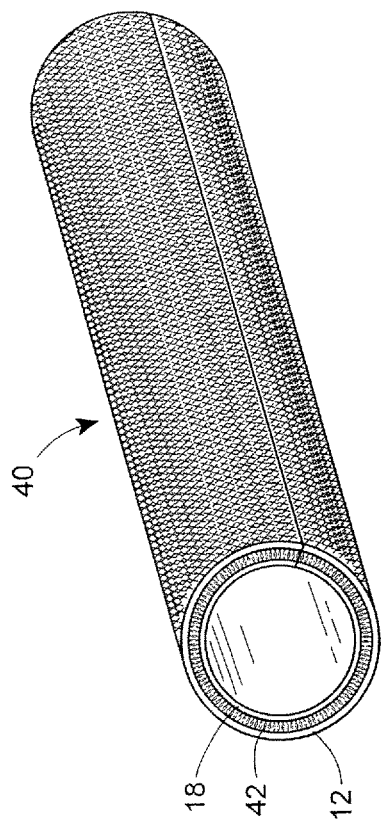
FIG. 7 is a perspective view of the heat-laminated film of FIG. 6, rolled into a cylindrical shape and sealed along a seam.

In another embodiment, shown in FIGS. 6-7, in order to provide reinforcement and avoid kinking or twisting of a catheter tube 40, a mesh or flexible scrim layer 42 may be included as an additional layer intermediate the first layer 12 and third layer 18 of the multi-layer catheter tube 40. The scrim layer 42 also provides the catheter tube 40 with shape memory, permitting the catheter tube 40 to collapse and recover to its cylindrical shape without any permanent deformation. Materials other than a scrim layer 42 may be utilized instead of or in addition to the scrim layer 42 to enhance structural integrity of the catheter tube 40, such as polymeric materials.

The material(s) forming the internal and/or external surfaces of the multi-layer catheter tube of the present disclosure preferably facilitate attachment and assembly of the catheter tube to peripheral components of fecal drainage and management systems, such as the Bowel Management System available from Hollister Incorporated of Libertyville, Ill., the assignee of the present disclosure. As such systems are intended for long-duration use, on the order of about twenty-nine days, it is advantageous to employ materials that will easily form a reliable bond, by adhesive and/or heat, between the catheter tube and the peripheral components, such as internal or external silicone balloons, catheter connections, such as to a collection bag or to a catheter tube extension, or plastic or metal ports, such as ports for providing endoscope access or for sampling fecal matter directly from the catheter tube, for the entire duration of use of the catheter.

As noted above, the advantages achieved by the odor barrier properties of the catheter tubes of the present disclosure would be negated, or significantly diminished, if fecal or flatus gasses could be transmitted through one or more walls of a collection bag 44 (see FIG. 8) to which the catheter tube 10 is connected. It is therefore desirable to use the multi-layer odor barrier catheter tube 10 in combination with a collection bag 44 having odor barrier walls. For example, each of the walls of the collection bag may include a barrier layer film such as the one disclosed in U.S. Pat. No. 7,270,860.

Figure 8:
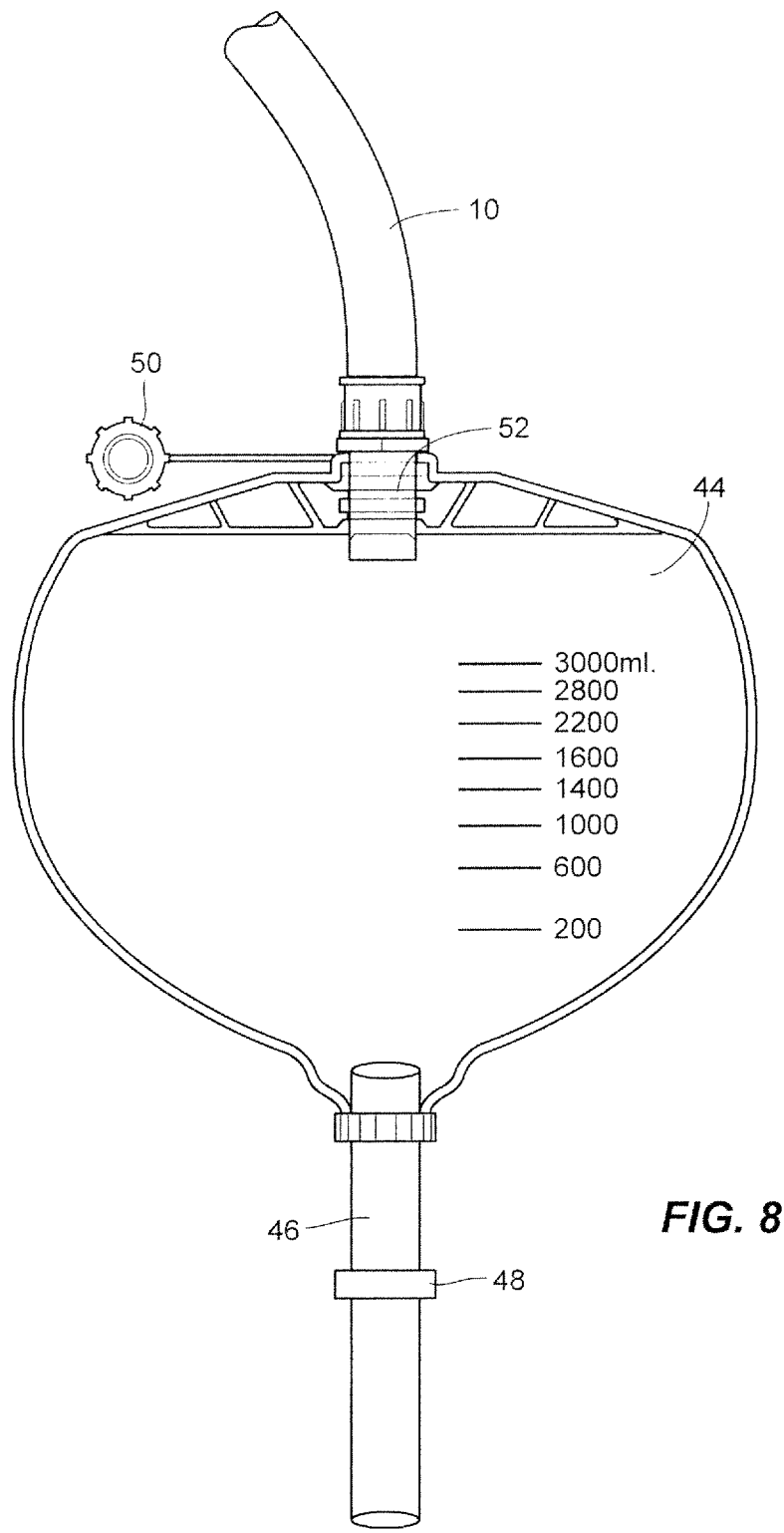
FIG. 8 is a front view of a combination of a multi-layer odor barrier catheter tube of the present disclosure in combination with a drainable collection bag having odor barrier walls.
Figure 9:
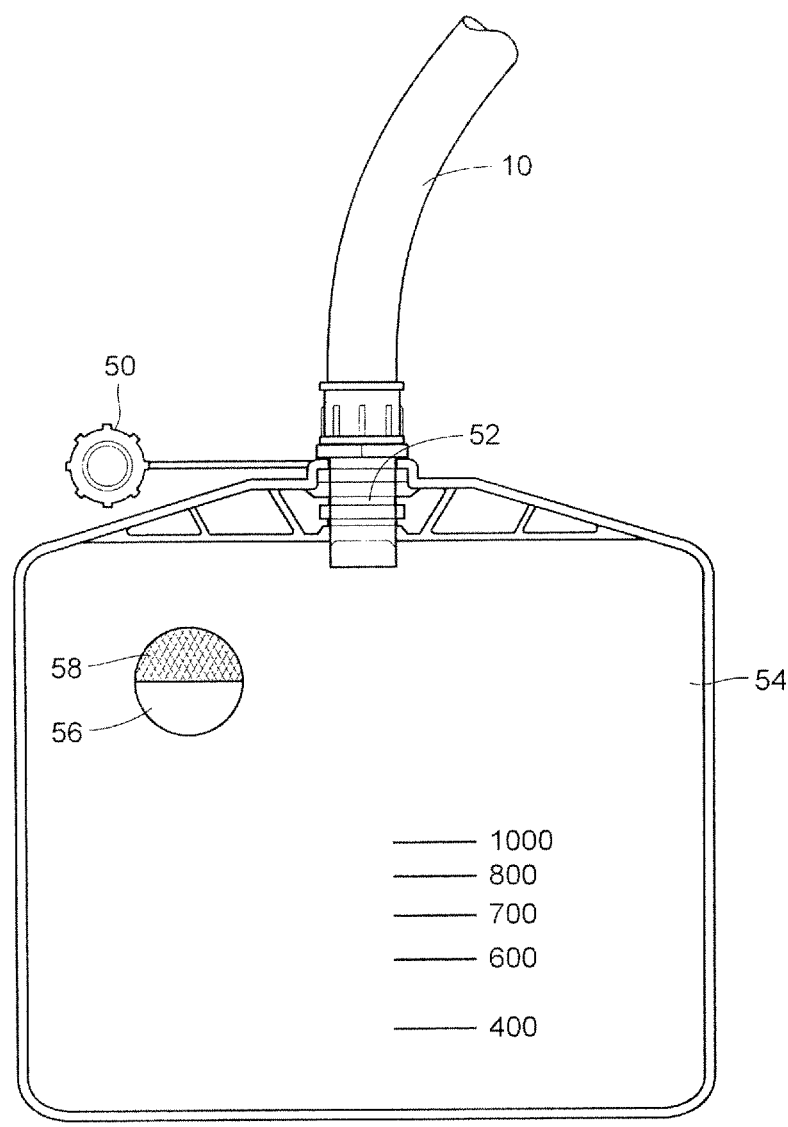
FIG. 9 is a front perspective view of a combination of a multi-layer odor barrier catheter tube of the present disclosure in combination with a closed, single-use collection bag having odor barrier walls.

The odor barrier collection bag may be a drainable collection bag 44, having a drainage tube 46 with a drainage tube stopper 48 and a cap 50 for capping a catheter tube connection port 52, as shown in FIG. 8. Alternately, the odor barrier collection bag may be a so-called "closed" collection bag 54, as illustrated in FIG. 9. A closed collection bag 54 is intended for single use, and preferably includes an integral vent 56 with a deodorizing filter 58.

While certain embodiments of multi-layer odor barrier catheter tubes, combinations of multi-layer odor barrier catheter tubes and odor barrier collection bags, and methods of manufacturing multi-layer odor barrier catheter tubes are disclosed herein, the appended claims are not intended to be limited thereto. Variations can be made to the disclosed embodiments that are still within the scope of the appended claims, literally or under the doctrine of equivalents.

We claim:

1. A fecal drainage system comprising:
   a collection bag having odor barrier walls; and
   a catheter tube connected to the collection bag and having at least two coextruded layers of material,
   wherein at least one of the layers includes an odor barrier material, and
   wherein a first of the layers defines an external surface of the catheter tube and is the layer including the odor barrier material, the first layer having a thickness 3 mils or less.

2. The fecal drainage system of claim 1, wherein a second layer adjacent to the first layer is thicker than the first layer and has a modulus of elasticity less than 100,000 psi when measured according to ASTM D882.

3. The fecal drainage system of claim 1, wherein an overall wall thickness of the catheter tube is in a range of about 10 mil to about 40 mil.

4. The fecal drainage system of claim 1, wherein an overall wall thickness of the catheter tube is in a range of about 25 mil to about 35 mil.

5. The fecal drainage system of claim 1, wherein the layer including the odor barrier material has a thickness less than 30% of a total wall thickness of the catheter tube.

6. The fecal drainage system of claim 1, wherein the catheter tube comprises at least three layers, wherein one of the at least three layers defines an external surface, one of the at least three layers defines an internal surface, and one of the at least three layers is an intermediate layer between the external surface and the internal surface, wherein the intermediate layer comprises a thermoplastic elastomer.

7. A fecal drainage system comprising:
   a collection bag having odor barrier walls; and
   a catheter tube connected to the collection bag and having
      a first layer defining an external surface of the catheter tube, the first layer including polyamide with odor barrier properties, and
      a second layer coextruded with the first layer.

8. The fecal drainage system of claim 7, wherein the second layer includes a hydrophilic material that becomes lubricious when exposed to liquid.

9. The fecal drainage system of claim 7, the first layer including a modulus-reducing modifier.

* * * * *